United States Patent [19]
Clem et al.

[11] Patent Number: 5,998,686
[45] Date of Patent: Dec. 7, 1999

[54] PROCESS FOR PRODUCING AROMATIC COMPOUNDS FROM ALIPHATIC HYDROCARBONS

[75] Inventors: Kenneth R. Clem, Humble; Gary D. Mohr, League City; Robert Scott Smith, Houston, all of Tex.

[73] Assignee: Exxon Chemical Patents Inc., Houston, Tex.

[21] Appl. No.: 08/865,631

[22] Filed: May 29, 1997

Related U.S. Application Data

[60] Provisional application No. 60/018,551, May 29, 1996.

[51] Int. Cl.$^6$ .............................. C07C 15/02; C07C 15/08
[52] U.S. Cl. .................... 585/415; 585/400; 585/407; 585/417; 585/418; 585/419; 585/420
[58] Field of Search ................................ 585/400, 407, 585/415, 417, 418, 419, 420

[56] References Cited

U.S. PATENT DOCUMENTS

| | | | |
|---|---|---|---|
| 4,582,815 | 4/1986 | Bowes | 502/64 |
| 4,652,360 | 3/1987 | Dessau | 585/415 |
| 4,746,763 | 5/1988 | Kocal | 585/417 |
| 4,847,224 | 7/1989 | Fajula et al. | 502/67 |
| 5,098,894 | 3/1992 | Sakurada et al. | 502/66 |
| 5,108,579 | 4/1992 | Casci | 585/418 |
| 5,460,796 | 10/1995 | Verduijn | 423/700 |

FOREIGN PATENT DOCUMENTS

| | | |
|---|---|---|
| 0284206 | 9/1988 | European Pat. Off. . |
| 0323892 | 1/1989 | European Pat. Off. . |
| 92/12928 | 8/1992 | WIPO . |
| WO96/16004 | 5/1996 | WIPO . |

*Primary Examiner*—Elizabeth D Wood
*Attorney, Agent, or Firm*—Edward F. Sherer

[57] ABSTRACT

A dehydrocyclo-oligomerization process is provided for converting aliphatic hydrocarbons to aromatics by contacting the feedstock under conversion conditions which a zeolite bound zeolite catalyst. The zeolite bound zeolite catalyst comprises first zeolite crystals which are bound together by second zeolite crystals. If the zeolite bound zeolite catalyst is selectivated, the process can produce greater than equilibrium amounts of paraxylene.

32 Claims, No Drawings

5,998,686

PROCESS FOR PRODUCING AROMATIC COMPOUNDS FROM ALIPHATIC HYDROCARBONS

This application claims benefit of Provisional application 60/018,551 filed May 29, 1996.

FIELD OF THE INVENTION

The present invention relates to a process using a zeolite bound zeolite catalyst for the production of aromatic hydrocarbons by the dehydrocyclo-oligomerization of aliphatic hydrocarbons.

BACKGROUND OF THE INVENTION

Dehydrocyclo-oligomerization is a process in which aliphatic hydrocarbons are reacted over a catalyst to produce a high yield of aromatics and hydrogen and certain byproducts. This process is distinct from the more conventional reforming where $C_6$ and higher carbon number reactants, primarily paraffins and naphthenes, are converted to aromatics. The aromatics produced by conventional reforming contain the same or a lesser number of carbon atoms per molecule than the reactants from which they were formed, indicating the absence of reactant oligomerization reactions. In contrast, the dehydrocyclo-oligomerization reaction results in an aromatic product that almost always contains more carbon atoms per molecule than the reactants, thus indicating that the oligomerization reaction is an important step in the dehydrocyclo-oligomerization process. Typically, the dehydrocyclo-oligomerization reaction is carried out at temperatures in excess of 260° C. using dual functional catalysts containing acidic and dehydrogenation components.

Aromatics, hydrogen, a $C_4$+ nonaromatics byproduct, and a light ends byproduct are all products of the dehydrocyclo-oligomerization process. The aromatics are the desired product of the reaction as they can be utilized as gasoline blending components or for the production of petrochemicals. Hydrogen is also a desirable product of the process. The hydrogen can be efficiently utilized in hydrogen-consuming refinery processes such as hydrotreating or hydrocracking processes. The least desirable product of the dehydrocyclo-oligomerization process is light ends byproducts. The light ends byproducts consist primarily of $C_1$ and $C_2$ hydrocarbons produced as a result of the hydrocracking side reactions.

Zeolites are crystalline microporous molecular sieves comprised of a lattice of silica and optionally alumina combined with exchangeable cations such as alkali or alkaline earth metal ions. Although the term "zeolites" includes materials containing silica and optionally alumina, it is recognized that the silica and alumina portions may be replaced in whole or in part with other oxides. For example, germanium oxide, tin oxide, phosphorous oxide, and mixtures thereof can replace the silica portion. Boron oxide, iron oxide, gallium oxide, indium oxide, and mixtures thereof can replace the alumina portion. Accordingly, the terms "zeolite", "zeolites" and "zeolite material", as used herein, shall mean not only materials containing silicon and, optionally, aluminum atoms in the crystalline lattice structure thereof, but also materials which contain suitable replacement atoms for such silicon and aluminum, such as galliumsilicates, silicoaluminophosphates (SAPO) and aluminophosphates (ALPO). The term "aluminosilicate zeolite", as used herein, shall mean crystalline zeolite materials consisting essentially of silicon and aluminum atoms in the crystalline lattice structure thereof.

Zeolites have been used in the past as a catalyst for the production of aromatic hydrocarbons by the dehydrocylco-oligomerization of aliphatic hydrocarbons. For example, U.S. Pat. No. 4,654,455 involves the production of aromatic hydrocarbons by the dehydrocylco-oligomerization of aliphatic hydrocarbons using a zeolite catalyst which contains gallium and an alumina binding material.

Synthetic zeolites are normally prepared by the crystallization of zeolites from a supersaturated synthesis mixture. The resulting crystalline product is then dried and calcined to produce a zeolite powder. Although the zeolite powder has good adsorptive properties, its practical applications are severely limited because it is difficult to operate fixed beds with zeolite powder. Therefore, prior to using in commercial processes, the zeolite crystals are usually bound.

The zeolite is typically bound by forming a zeolite aggregate such as a pill, sphere, or extrudate. The extrudate is usually formed by extruding the zeolite in the presence of a non-zeolitic binder and drying and calcining the resulting extrudate. The binder materials used are resistant to the temperatures and other conditions, e.g., mechanical attrition, which occur in various hydrocarbon conversion processes. Examples of binder materials include amorphous materials such as alumina, silica, titania, and various types of clays. It is generally necessary that the zeolite be resistant to mechanical attrition, that is, the formation of fines which are small particles, e.g., particles having a size of less than 20 microns.

Although such bound zeolite aggregates have much better mechanical strength than the zeolite powder, when such a bound zeolite is used for the dehydrocyclo-oligomerization of aliphatic hydrocarbons, the performance of the catalyst, e.g., activity, selectivity, activity maintenance, or combinations thereof, can be reduced because of the binder. For instance, since the amorphorous binder is typically present in an amount of up to about 50 wt. % of zeolite, the binder dilutes the adsorptive properties of the zeolite aggregate. In addition, since the bound zeolite is prepared by extruding or otherwise forming the zeolite with the binder and subsequently drying and calcining the extrudate, the amorphous binder can penetrate the pores of the zeolite or otherwise block access to the pores of the zeolite, or slow the rate of mass transfer to the pores of the zeolite which can reduce the effectiveness of the zeolite when used in hydrocarbon conversion processes. Furthermore, when such a bound zeolite is used in catalytic conversions processes such as the dehydrocyclo-oligomerization of aliphatic hydrocarbon, the binder may affect the chemical reactions that are taking place within the zeolite and also may itself catalyze undesirable reactions which can result in the formation of undesirable products.

SUMMARY OF THE INVENTION

The present invention is directed process for producing aromatic hydrocarbons by the dehydrocyclo-oligomerization of aliphatic hydrocarbons. The process comprises contacting a feedstream containing aliphatic hydrocarbons under aromatization conditions with a zeolite bound zeolite catalyst which contains first crystals of an acidic intermediate pore size first zeolite and second crystals of a second zeolite which binds together the first zeolite crystals.

In another embodiment of the present invention, there is provided a process for the dehydrocyclo-oligomerization of aliphatic hydrocarbons using the zeolite bound zeolite catalyst to produce a product which includes xylenes which are enriched in paraxylene.

DETAILED DESCRIPTION OF THE INVENTION

The zeolite bound zeolite catalyst used in the process of the present invention comprises first crystals of a acidic intermediate pore size first zeolite and a binder comprising second crystals of a second zeolite. The use of second zeolite crystals as a binder results in a catalyst which provides a means for controlling undesirable reactions taking place on or near the surface of the first zeolite crystals and can have improved mass transfer of reactants and greater access to and from the pores of the zeolite.

Unlike zeolite catalysts bound with amorphous material such as silica or alumina to enhance the mechanical strength of the zeolite, the zeolite bound zeolite catalyst used in the process of the present invention does not contain significant amounts of non zeolitic binders. Preferably, the zeolite bound zeolite catalyst contains less than 10 percent by weight based on the total weight of the first and second zeolite of non-zeolitic binder, more preferably contains less than 5 percent by weight, and, most preferably, the first and second zeolite are substantially free of non-zeolitic binder. Preferably, the second zeolite crystals bind the first zeolite crystals by adhering to the surface of the first zeolite crystals thereby forming a matrix or bridge structure which also holds the first crystals particles together. More preferably, the second zeolite crystals bind the first zeolite by intergrowing so as to form a coating or partial coating on the larger first zeolite crystals and, most preferably, the second zeolite crystals bind the first zeolite crystals by intergrowing to form an attrition resistant over-growth over the first zeolite crystals.

Although the invention is not intended to be limited to any theory of operation, it is believed that one of the advantages of the zeolite bound zeolite catalyst when used in the process of the present invention is obtained by the crystals of the second zeolite controlling the accessibility of the acid sites on the external surfaces of the first zeolite to reactants. Since the acid sites existing on the external surface of a zeolite catalyst are not shape selective, these acid sites can adversely affect reactants entering the pores of the zeolite and products exiting the pores of the zeolite. In line with this belief, since the acidity of the second zeolite can be carefully selected, the second zeolite does not significantly adversely affect the reactants exiting the pores of the first zeolite which can occur with conventionally bound zeolite catalysts and may beneficially affect the aromatic selectivity of a dehydrogenation process and also the reactants exiting the pores of the first zeolite. Still further, since the second zeolite is not amorphous but, instead, is a molecular sieve, hydrocarbons have increased access to the pores of the first zeolite during the aromatization process.

The terms "acidity", "lower acidity" and "high acidity" as applied to zeolite are know to persons skilled in the art. The acidic properties of zeolite are well known. However, with respect to the present invention, a distinction must be made between acid strength and acid site density. Acid sites of a zeolite can be a Bronstead acid or a Lewis acid. The density of the acid sites and the number of acid sites are important in determining the acidity of the zeolite. Factors directly influencing the acid strength are (i) the chemical composition of the zeolite framework, i.e., relative concentration and type of tetrahendral atoms, (ii) the concentration of the extra-framework cations and the resulting extra-framework species, (iii) the local structure of the zeolite, e.g., the pore size and the location, within the crystal or at/near the surface of the zeolite, and (iv) the pretreatment conditions and presence of co-adsorbed molecules. The amount of acidity is related to the degree of isomorphous substitution provided, however, such acidity is limited to the loss of acid sites for a pure $SiO_2$ composition. As used herein, the terms "acidity", "lower acidity" and "higher acidity" refers to the concentration of acid sites irregardless of the strength of such acid sites which can be measured by ammonia adsorption.

The first zeolite used in the zeolite bound zeolite catalyst is an intermediate pore size zeolite. Intermediate pore size zeolites have a pore size from about 5 to about 7 Å and include, for example, AEL, MFI, MEL, MFS, MEI, MTW, EUO, MTT, HEU, FER, and TON structure type zeolites. These zeolites are described in "Atlas of Zeolite Structure Types", eds. W. H. Meier and D. H. Olson, Butterworth-Heineman, Third Edition, 1992, which is hereby incorporated by reference. Examples of specific intermediate pore size zeolites include ZSM-5, ZSM-11, ZSM-12, ZSM-22, ZSM-23, ZSM-34, ZSM-35, ZSM-38, ZSM-48, ZSM-50, and ZSM-57. Preferred first zeolites are SAPO-11, gallium-silicate zeolites having an MFI structure, and aluminosilicate zeolites having an MFI structure.

The term "average particle size" as used herein, means the average diameter of the crystals, e.g., number average of the major axis and minor axis.

The average crystal size of the crystals of the first zeolite is preferably from about 0.1 micron to about 15 microns, more preferably from about 1 to about 6 microns.

Procedures to determine crystal size are know to persons skilled in the art. For instance, crystal size may be determined directly by taking a suitable scanning electron microscope (SEW) picture of a representative sample of the crystals.

Intermediate pore size first zeolites will generally comprise a composition having the following molar relationship:

$$X_2O_3:(n) YO_2,$$

wherein X is a trivalent element such as aluminum and gallium and Y is a tetravalent element such as silicon, tin, and/or germanium; and n has a value greater than 12, said value being dependent upon the particular type of zeolite. When the intermediate pore size zeolite is a MFI structure type zeolite, n is preferably greater than 20.

As known to persons skilled in the art, the acidity of a zeolite can be reduced using many techniques such as by steaming. In addition, the acidity of a zeolite is dependent upon the form of the zeolite with the hydrogen form having the highest acidity and other forms of the zeolite such as the sodium form having less acidity than the acid form.

Accordingly, the mole ratios of silica to alumina and silica to gallia disclosed herein shall include not only zeolites having the disclosed mole ratios, but shall also include zeolites not having the disclosed mole ratios but having equivalent catalytic activity.

When the first zeolite is an aluminosilicate zeolite, the first zeolite will preferably have a silica to alumina mole ratio from 20:1 to 300:1. More preferably, the first zeolite will have a silica to alumina mole ratio of from about 30:1 to about 150:1.

When the first zeolite is a gallium silicate zeolite, the zeolite preferably comprises a composition having the following molar relationship:

$$Ga_2O_3:ySiO_2$$

wherein y is between about 24 and about 500. The zeolite framework may contain only gallium and silicon atoms or may also contain a combination of gallium, aluminum, and silicon. When the first zeolite is a MFI structure type gallium silicate zeolite, the second zeolite will preferably be an intermediate pore size zeolite having a silica to gallia mole ratio greater than 100. The second zeolite can also have higher silica to gallia mole ratios, e.g., greater than 200, 500, 1000, etc.

The second zeolite will usually have an intermediate pore size and have less acid activity then the first zeolite. Preferably, the second zeolite will be substantially non-acidic and will have the same structure type as the first zeolite. The preferred second zeolites are ALPO-11 and aluminosilicate zeolites having a silica to alumina mole ratio greater than 100 such as low acidity ZSM-5. If the second zeolite is an aluminosilicate zeolite, the second zeolite will generally have a silica to alumina mole ratio greater than 200:1, e.g., 500:1; 1,000:1, etc., and in some applications will contain no more than trace amounts of alumina. The second zeolite can also be silicalite, i.e., a AM type substantially free of alumina, or silicalite 2, a MEL type substantially free of alumina. The second zeolite is usually present in the zeolite bound zeolite catalyst in an amount in the range of from about 10% to 60% by weight based on the weight of the first zeolite and, more preferably, from about 20% to about 50% by weight.

The second zeolite crystals preferably have a smaller size than the first zeolite crystals and more preferably will have an average particle size of less than 1 micron, and most preferably will have an average particle size from about 0.1 to about 0.5 micron. The second zeolite crystals, in addition to binding the first zeolite particles and maximizing the performance of the catalyst will preferably intergrow and form an over-growth which coats or partially coats the first zeolite crystals. Preferably, the crystals will be resistant to attrition.

The zeolite bound zeolite catalyst used in the process of the present invention will usually contain a metal component selected from the elements of Groups IIB through IVB of the Periodic Table of the Elements (IUPAC). Examples of such metals include gallium, zinc, and tin. The metal component may be present in any form including elemental metal, oxide, hydroxide, halide, oxyhalide, or in chemical combination with one or more of the other ingredients of the zeolite bound zeolite catalyst. It is believed that the best results are obtained when the metal component is in the zero valency state. The metal component can be used in any amount which is catalytically effective. Generally, the zeolite bound zeolite catalyst will contain on an elemental basis from about 0.5 to about 5% of the metal based on the weight of the zeolite bound zeolite catalyst. The metal component preferably comprises gallium.

The metal component may be incorporated into the zeolite bound zeolite catalyst in any suitable manner known to the art such as by ion exchange or impregnation. Additionally, the metal component may be surface impregnated such that the majority of the metal is located on the outer portion of the zeolite by means such as physical mixing by chemical complexing, or by pore blockage prior to impregnation of the metal. It is intended to include within the scope of the present invention all conventional methods for incorporating and simultaneously distributing either uniformly or non-uniformly a metallic component in zeolite bound zeolite catalyst. One method of incorporating the metal involves ion exchange of the active catalytic component with a soluble, decomposable compound of the metal such as, with respect to gallium, gallium tribromide, gallium perchlorate, gallium trichloride, gallium hydroxide, gallium nitrates, gallium oxalate, and the like compounds. Another method of incorporating the gallium into the zeolite bound zeolite catalyst is to convert the silica of a silica bound aggregate containing said first zeolite and the metal to the second zeolite.

The zeolite bound zeolite catalyst used in the process of the present invention is preferably prepared by a three step procedure which is described for a first ZSM-5 zeolite and a high silica MFI structure type second zeolite. The first step involves the synthesis of the first zeolite crystals prior to converting it to the zeolite bound zeolite catalyst. Processes for preparing the first zeolite are known in the art. For example, with respect to the preparation of a MFI type aluminosilicate zeolite, a preferred process comprises preparing a solution containing tetrapropyl ammonium hydroxide or bromide, alkali metal oxide, an oxide of aluminum, an oxide of silicon and water, and then heating the reaction mixture to a temperature of 80° C. to 200° C. for a period of from about four hours to eight days. The resulting gel forms solid crystal particles which are separated from the reaction medium, washed with water and dried. The resulting product may then be optionally calcined in air at temperatures of 400–550° C. for a period of 10–40 hours to remove tetrapropylammonium (TPA) cations.

Next, a silica-bound aluminosilicate zeolite can be prepared preferably by mixing a mixture comprising the aluminosilicate zeolite crystals, a silica gel or sol, water and optionally an extrusion aid and, optionally alumina or gallium and, optionally, the metal component until a homogeneous composition in the form of an extrudable paste develops. The silica binder used in preparing the silica bound zeolite aggregate is preferably a silica sol and preferably contains only very minor amounts of alumina or gallium, e.g., less than 2,000 ppm. The amount of silica used is such that the content of the zeolite in the dried extrudate will range from about 40 to 90% by weight, more preferably from about 50 to 80% by weight, with the balance being primarily silica, e.g. about 20 to 50% by weight silica.

The resulting paste can be molded, e.g. extruded, and cut into small strands, e.g., approximately 2 mm diameter extrudates, which can be dried at 100–150° C. for a period of 4–12 hours and then calcined in air at a temperature of from about 400° C. to 550° C. for a period of from about 1 to 10 hours.

Optionally, the silica-bound aggregate can be made into a very small particles which have application in fluid bed processes such as catalytic cracking. This preferably involves mixing the zeolite with a silica containing matrix solution so that an aqueous solution of zeolite and silica binder is formed which can be sprayed dried to result in small fluidizable silica-bound aggregate particles. Procedures for preparing such aggregate particles are known to persons skilled in the art. An example of such a procedure is described by Scherzer (Octane-Enhancing Zeolitic FCC Catalysts, Julius Scherzer, Marcel Dekker, Inc. New York, 1990). The fluidizable silica-bound aggregate particles, like the silica bound extrudates described above, would then undergo the final step described below to convert the silica binder to a second zeolite.

The final step in the three step catalyst preparation process is the conversion of the silica present in the silica-bound catalyst to a second zeolite which serves to bind the first zeolite crystals together. The first zeolite crystals are thus held together without the use of a significant amount of non-zeolite binder. To prepare the zeolite bound zeolite catalyst, the silica-bound aggregate can be first aged in an appropriate aqueous solution at an elevated temperature. Next, the contents of the solution and the temperature at which the aggregate is aged should be selected to convert the amorphous silica binder into the second zeolite. It is preferable that the second zeolite be of the same type as the first zeolite. The newly-formed zeolite is produced as crystals. The crystals may grow on and/or adhere to the initial zeolite crystals, and may also be produced in the form of new intergrown crystals, which are generally much smaller than the initial crystals, e.g., of sub-micron size. These newly formed crystals may grow together and interconnect.

The nature of the aluminosilicate zeolite formed in the secondary synthesis conversion of the silica to zeolite may vary as a function of the composition of the secondary synthesis solution and synthesis aging conditions. The secondary synthesis solution is preferably an aqueous ionic solution containing a source of hydroxyl ions sufficient to convert the silica to the desired zeolite.

The zeolite bound zeolite catalyst is usually in the acidic or partially neutralized acidic form. One method of obtaining the acidic form is to ion exchange the zeolite to produce the ammonium salt form. As a result of calcination, the acid form of the zeolite bound zeolite catalyst is produced.

The zeolite bound zeolite catalyst can be selectivated to improve its paraxylene selectivity to thereby produce a resulting xylene para- xylene rich fraction. Compounds suitable for selectivating to the zeolite bound zeolite catalyst include silicon compounds.

The silicon compounds may comprise a polysiloxane including silicones, a siloxane, and a silane including disilanes and alkoxysilanes.

Silicone compounds which can be used in the present invention can be characterized by general formula:

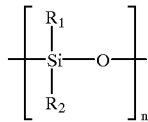

wherein $R_1$ is hydrogen, fluoride, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, and n is an integer of at least 2 and generally in the range of 2 to 1000. The molecular weight of the silicone compound employed is generally between 80 and 20,000 and preferably 150 to 10,000. Representative silicone compounds included dimethylsilicone, diethylsilicone, phenylmethylsilicone, methyl hydrogensilicone, ethylhydrogensilicone, phenylhydrogensilicone, methylethylsilicone, phenylethylsilicone, diphenylsilicone, methyltri fluoropropylsilicone, ethyltrifluoropropylsilicone, tetrachlorophenyl methyl silicone, tetrachlorophenylethyl silicone, tetrachloro phenylhydrogen silicone, tetrachlorophenylphenyl silicone, methylvinylsilicone and ethylvinylsilicone. The silicone compound need not be linear but may be cyclic as for example hexamethylcyclotrisiloxane, octamethylcyclotetrasiloxane, hexaphenyl cyclotrisiloxane and octaphenylcyclotetrasiloxane. Mixtures of these compounds may also be used as well as silicones with other functional groups.

Useful siloxanes or polysiloxanes include as non-limiting examples hexamethylcyclotrisiloxane, octamethylcyclotetrasiloxane, decamethyl cyclopentasiloxane, hexamethyldisiloxane, octamethytrisiloxane, decamethyltetrasiloxane, hexaethylcydotrisiloxane, octaethylcyclo tetrasiloxane, hexaphenylcyclotrisiloxane and octaphenylcyclo tetrasiloxane.

Useful silanes, disilanes, or alkoxysilanes include organic substituted silanes having the general formula:

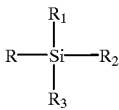

wherein R is a reactive group such as hydrogen, alkoxy, halogen, carboxy, amino, acetamide, trialkylsilyoxy, $R_1$, $R_2$ and $R_3$ can be the same as R or can be an organic radical which may include alkyl of from 1 to 40 carbon atoms, alkyl or aryl carboxylic acid wherein the organic portion of the alkyl contains 1 to 30 carbon atoms and the aryl group contains 6 to 24 carbon which may be further substituted, alkylaryl and arylalkyl groups containing 7 to 30 carbon atoms. Preferably, the alkyl group for an alkyl silane is between 1 and 4 carbon atoms in chain length. Mixtures may also be used.

The silanes or disilanes include, as non-limiting examples, dimethylphenylsilane, phenytrimethylsilane, triethylsilane and hexa methyldisilane. Useful alkoxysilanes are those with at least one silicon-hydrogen bond.

The zeolite bound zeolite catalyst can be preselectivated with the organosilicone compounds by depositing the compounds on the catalyst or the catalyst can be selectivated with the organosilicone compound by feeding the selectivating agent simultaneously with the feed stream at 5 conditions of a temperature from 100° C. to 600° C., a pressure of 1 to 2000 psig, a weight hour space velocity of 0.1 to 100.

The dehydrocyclo-oligomerization conditions employed in the process of the present invention will vary depending on such factors as feedstock composition and desired conversion. A desired range of conditions for the dehydrocyclodimerization of the aliphatic hydrocarbons to aromatics include a temperature from about 350° C. to about 650° C., a pressure from about 1 to about 20 atmospheres, and weight hour space velocity from about 0.2 to about 5. The preferred process conditions are a temperature in the range from about 850° F. to about 1250° F., a pressure in or about the range from atmospheric to 400 psig, and a WHSV of 1 to 5. It is understood that, as the average carbon number of the feed increases, a temperature in the lower end of temperature range is required for optimum performance and conversely, as the average carbon number of the feed decreases, the higher the required reaction temperature.

The feed stream used in the dehydrocyclo-oligomerization process of the present invention will preferably contain at least one aliphatic hydrocarbon containing 2 to about 6 carbon atoms. The aliphatic hydrocarbons may be open chain, straight chain, or cyclic. Examples such as hydrocarbons include ethane propane, propylene, n-butane, n-butenes, isobutane, straight and branch hexanes, and hexenes. Preferably, the hydrocarbons $C_3$ and/or $C_4$ are selected from isobutane, normal butane, isobutene, normal butene, isopropane, propane, and propylene. Diluents, refractory or reactant in nature, may also be included in the feed stream. Examples of such diluents include hydrogen, nitrogen, helium, argon, neon, CO, $CO_2$, $H_O$ or a water precursor, i.e., compounds which liberate $H_O$ when heated to dehydrocyclo-oligomerization reaction temperatures. Methane may also be a component of the feedstock of the present invention.

It is anticipated that the $C_2$–$C_6$ aliphatic hydrocarbon feedstream utilized in the process of the instant invention may originate as a product or by-product of a refinery or petrochemical process. The light aliphatic hydrocarbons produced and recovered in a cracking or a reforming process would be examples of such process derived feed streams. The products of a synthesis gas production process is another potential source of feed for the instant process. Another anticipated source of feed is the light aliphatic hydrocarbons recovered at the well head at oil production facilities.

The following examples illustrate the invention.

EXAMPLE 1

Preparation Procedure for Catalyst A–D

I. Catalyst A

A catalyst comprising ZSM-5 (75:1 silica to alumina mole ratio) which was bound by 30% by weight amorphorous silica was treated three times at 70° C. with a 5 fold weight excess of 1.0 normal aqueous ammonium nitrate. The treated extrudates were washed until the wash water had a conductivity of less than 10 µS/cm, dried overnight at 100° C. and then cooled with nitrogen. The extrudates were impregnated with 20 wt. percent aqueous gallium nitrate solution until incipient wetness was achieved. The product was maintained at room temperature for 4 hours in air. Next, the product was dried in air for 1 hour at 88° C. in air and then calcined by heating from 35° C. to 510° C. in 3½ hours and holding at 510° C. for 10 hours. The atomic gallium content of the catalyst was 1.92 wt. %. The catalyst is identified in the tables as Catalyst A.

II. Catalyst B

A catalyst comprising H-ZSM-5 core crystals having a silica to alumina mole ratio of 75:1 and bound by 30% by weight ZSM-5 binder crystals having a silica to alumina mole ratio of 900:1 was prepared by first mixing the ZSM-5 core crystals with amorphous silica containing a small amount of alumina and then forming the mixture into a silica bound extrudate. Next, the silica binder of the extrudate was converted to the second zeolite by aging the aggregate at elevated temperatures in an aqueous solution containing a template and a source hydroxy ions sufficient to convert the silica to the binder crystals. The resulting zeolite bound zeolite was then washed, dried, and calcined. Prior to use, the catalyst was dried overnight at 100° C. and then cooled to room temperature under nitrogen. The resulting material was impregnated with gallium in the manner as described in above. The atomic gallium content of the catalyst was 1.95 wt. %.

III. Catalyst C

A catalyst comprising Na-ZSM-5 core crystals having a silica to alumina mole ratio of 75:1 and bound by 30% by weight MFI structure type zeolite crystals having a silica to gallia mole ratio of 70:1 was prepared by first mixing the ZSM-5 core crystals with amorphous silica containing gallia and then forming the mixture into a silica bound extrudate. Next, the silica binder of the extrudate was converted to the second zeolite by aging the aggregate at elevated temperatures in an aqueous solution containing a template and a source hydroxy ions sufficient to convert the silica to a binder crystal. The resulting zeolite bound zeolite was then washed, dried, and calcined. Prior to use, the catalyst was treated three times at 70° C. with a 5 fold weight excess of a 1.0 normal aqueous ammonium nitrate solution. The resulting product was washed until the spent wash water had a conductivity of less than 10 micro-Siemens. The product was dried overnight in air and calcined by heating. The atomic gallium content of the catalyst was 0.87 wt. %.

IV. Catalyst D

Gallium was incorporated into a catalyst comprising ZSM-5 (80:1 silica to alumina mole ratio) bound by 20% by weight amorphous alumina using the procedure described in I. The atomic gallium content of the catalyst was 2.37 wt. %.

EXAMPLE 2

Catalysts A–D were tested for the aromatization of propane. The catalysts were crushed and sized between 30 U.S. mesh and +40 U.S. mesh sieves. An amount of 1.5 grams of each catalyst was mixed with 3 grams of 14/20 mesh sized quartz chips and packed into a tubular reactor. The catalysts were treated for 1 hour at 584° C. with 50 mole/h $H_2$ diluted with 95% vol. $N_2$. The aromatization conditions used in the tests were 550° C., a propane weight hour space velocity (WHSV) of 2 and a pressure of 0.7 psig. Gas chromatography was used for analysis of the resulting products. The propane conversion and yield of $C_6$–$C_8$ aromatics and $C_1$–$C_2$ are shown below in Table I.

TABLE I

| Catalyst | Time on Stream (hr) | $C_3$ Conv (%) | $C_6$–$C_8$ Aromatics Yield (%) | $C_1$–$C_2$ Yield (%) |
|---|---|---|---|---|
| A. | 8.67 | 63.5 | 35.5 | 11.5 |
| B. | 3.92 | 51.6 | 49.2 | 29.5 |
| C. | 6.68 | 46.1 | 35.7 | 34.8 |
| D. | 3.33 | 89.2 | 15.6 | 2.2 |

Catalysts B and C were able to achieve high aromatics conversion. The performance of Catalyst C was achieved even though it contained about 50 wt. % less gallium than Catalysts B and C.

Example 3

Catalysts A–D were tested for deactivation using the conditions of Example 2, except that for Catalysts B and C, the WHSV was 1.0 and the pressure was 0.2 psig. The propane conversion was monitored over time and a first order rate constant for catalyst deactivation was calculated as the slope of the line from plotting $-\ln(\ln(1/1-x))$ versus time, where x is the fractional propane conversion. The wt. % of coke in-run time was determined by dividing the amount of coke in the catalyst by catalyst run time. The run times were: Catalyst A—43 hours, Catalyst B—114 hours, Catalyst C—52 hours, and Catalyst D—91 hours. The results are shown in Table II.

TABLE II

| Catalyst | Deactivation k obs (1/hr) | Wt. % Coke per hour run time |
|---|---|---|
| A | 0.026 | 0.082 |
| B | 0.017 | 0.057 |
| C | 0.031 | 0.142 |
| D | 0.055 | 0.132 |

One of the benefits of the present invention is that of the zeolite bound zeolite catalyst deactivates slower than conventionally bound zeolite catalysts with an equivalent amount of gallium. The data shows that the deactivation rate for Catalyst B was at least 35% less than Catalyst A.

Example 4

Catalyst B was selectivated with hexamethyldisiloxane A S) by heating the catalyst to 500–599° C. and then contacting it with a feed containing toluene and 1 wt. % HMDS at a WHSV of 4.1 and pressure of 1 psig. The feed had a hydrogen to toluene mole ratio of 2:1. Toluene conversions are shown below in Table III:

TABLE III

| Time (hr) | Temp (° C.) | Tol Conv (%) | Benzene to Xylene Mole Ratio | p-Xylene Selectivity (%) |
|---|---|---|---|---|
| 1.38 | 500 | 3.35 | 0.63 | 62.0 |
| 3.13 | 525 | 4.48 | 0.58 | 63.2 |
| 5.18 | 599 | 11.6 | 0.63 | 60.6 |
| 8.12 | 599 | 7.1 | 0.74 | 69.4 |
| 10.59 | 599 | 5.8 | 0.72 | 76.1 |
| 13.05 | 599 | 4.87 | 0.71 | 78.8 |

*PX selectivity = (PX/[PX + MX + OX]) × 100

After selectivation, treated Catalyst B (identified in Table IV below as B-T) and untreated Catalyst B were tested for propane aromatization. The conditions were 550° C., WHSV of 1.0 and a pressure of 0.2. The results of these tests are shown below in Table IV.

TABLE IV

| Catalyst | Time on Stream (hr) | $C_3$ Conv (%) | $C_6$–$C_8$ Aromatics Yield (%) | $C_1$–$C_2$ Yield (%) | Xylene Yield (%) | p-Xylene Selectivity (%) |
|---|---|---|---|---|---|---|
| B | 4.75 | 69.8 | 40.9 | 26.3 | 7.2 | 28.3 |
| B-T | 0.52 | 37 | 41.7 | 26.9 | 7.9 | 59.5 |
| B-T | 10.05 | 32.3 | 42.5 | 24.4 | 9.1 | 55.5 |
| B-T | 19.58 | 28.3 | 46.7 | 20.4 | 10.0 | 52.6 |
| B-T | 29.17 | 20.5 | 48.1 | 24.3 | 10.6 | 55.7 |
| B-T | 38.72 | 17.3 | 47.1 | 24.8 | 10.6 | 56.7 |
| B-T | 48.3 | 13.8 | 47.2 | 27.3 | 10.1 | 59.5 |
| B-T | 61.05 | 11 | 46.3 | 29.4 | 10.0 | 61.9 |

As shown in the tests, the zeolite bound zeolite catalyst exhibits good $C_6$–$C_8$ aromatics selectivity and when selectivated, the process can produce a product stream having enriched amounts of para-xylene with respect to other isomers of xylene.

What is claimed is:

1. A process for the production of aromatic hydrocarbons by the dehydrocyclo-oligomerization of aliphatic hydrocarbons which comprises contacting a feedstream containing aliphatic hydrocarbons under dehydrocyclo-oligomerization conditions with a zeolite bound zeolite catalyst which comprises:
   (a) first crystals of an intermediate pore size first zeolite having acid activity; and,
   (b) a binder comprising of second crystals of a second zeolite having less acid activity than the first zeolite[.];
   wherein said zeolite bound zeolite catalyst contains less than about 10 percent by weight of non-zeolitic binder based on the weight of said first zeolite and said second zeolite.

2. The process recited in claim 1, wherein said second crystals form at least a partial coating on said first crystals.

3. The process recited in claim 2, wherein said first crystals of said first zeolite have an average particle size greater than about 0.1 micron and said second crystals of said second zeolite have an average particle size that is less than the average particle size of said first crystals of said first zeolite.

4. The process recited in claim 3, wherein said first zeolite has a structure selected from the group consisting of AEL, MFI, MEL, MTW, MTT, FER, TON, and EUO.

5. The process recited in claim 4, wherein said second zeolite is an intermediate pore size zeolite.

6. The process recited in claim 5, wherein said catalyst additionally contains at least one metal component selected from the group consisting of Groups IIB–IVB of the Periodic Table of Elements.

7. The process recited in claim 6, wherein said at least one metal component is gallium.

8. The process recited in claim 7, wherein the dehydrocyclodimerization conditions comprise a temperature in the range from about 350° to about 650° C., a pressure from about 1 to 20 atoms, a liquid hourly space velocity of from about 0.2 to 5 liquid volumes of said aliphatic hydrocarbons per hour per volume of said catalyst composition.

9. The process recited in claim 4, wherein the structure of said second zeolite is the same as said first zeolite.

10. The process recited in claim 6, wherein said aliphatic hydrocarbons have from about 2 to about 6 carbon atoms.

11. The process recited in claim 10, wherein said first zeolite and said second zeolite are an aluminosilicate zeolite or a gallium silicate zeolite.

12. The process recited in claim 11, wherein said first zeolite is an aluminosilicate zeolite having a silica to alumina mole ratio of from about 20:1 to about 300:1.

13. The process recited in claim 12, wherein said second zeolite has a silica to alumina mole ratio greater than about 200:1.

14. The process recited in claim 13, wherein said aliphatic hydrocarbons are selected from the group consisting of isobutane, normal butane, isobutene, normal butene, propane and propylene.

15. The process recited in claim 14, wherein said first zeolite has an MFI structure.

16. The process recited in claim 13, wherein said second zeolite is has a MFI or MEL structure.

17. The process recited in claim 15, wherein said second zeolite is silicalite or silicalite 2.

18. The process recited in claim 16, wherein the average particle size of the crystals of said first zeolite is from about at least 1 to about 6 microns and the average particle size of the crystals of said second zeolite is from about 0.1 to about 0.5 microns.

19. The process recited in claim 11, wherein said zeolite bound zeolite catalyst is prepared by converting at sufficient temperature the silica binder of a silica-bound aggregate containing said first crystals of said first zeolite in an aqueous ionic solution containing hydroxy ions.

20. The process recited in claim 16, wherein paraxylene selectivity of said zeolite bound zeolite catalyst is enhanced by depositing a silicon compound on said catalyst.

21. The process recited in claim 20, wherein said silicon compound is hexamethyldisiloxane.

22. The process recited in claim 20, wherein said process produces a product containing greater than equilibrium amounts of para-xylene.

23. The process recited in claim 20, wherein said feed comprises propane.

24. The process recited in claim 3, wherein said first zeolite is SAPO-11.

25. The process recited in claim 24, wherein said second zeolite is ALPO-11.

26. The process recited in claim 2, wherein said zeolite bound zeolite catalyst contains less than 5% by weight of non-zeolitic binder based on weight of said first zeolite and said second zeolite.

27. The process recited in claim 2 wherein said first zeolite is selected from the group consisting of ZSM-5, ZSM-11, ZSM-12, ZSM-22, ZSM-23, ZSM-34, ZSM-35, ZSM-38, ZSM-48, ZSM-50, ZSM-57, SAPO-1 1, and galliumsilicate zeolite having an MFI structure.

28. The process recited in claim 27, wherein said first crystals have an average particle size of from about I to about 6 microns.

29. The process recited in claim 28, wherein said second crystals have an average particle size of from about 0.1 to about 0.5 microns.

30. The process recited in claim 2, wherein said first zeolite is a gallium silicate zeolite having a silica to gallia mole ratio from about 24 to about 500.

31. The process recited in claim 3, wherein said second zeolite is a gallium silicate zeolite having a silica to gallia mole ratio greater than 100.

32. The process recited in claim 2, wherein said second zeolite is ALPO-11 or MFI structure zeolite and said first zeolite is SAPO-11 or MFI structure zeolite.

* * * * *